United States Patent [19]
Samuelsson

[11] Patent Number: 6,013,066
[45] Date of Patent: Jan. 11, 2000

[54] ABSORBENT ARTICLE FOR ATTACHMENT TO A BOXER SHORT OR A PANTY

[75] Inventor: Ann Samuelsson, Lindome, Sweden

[73] Assignee: SCA Mölnycke AB, Gothenburg, Sweden

[21] Appl. No.: 08/924,831

[22] Filed: Sep. 5, 1997

[30] Foreign Application Priority Data

Sep. 9, 1996 [SE] Sweden ................................. 9603273

[51] Int. Cl.⁷ .................................................. A61F 13/15
[52] U.S. Cl. .......................... 604/387; 604/386; 604/389
[58] Field of Search ................................. 604/385.1, 386, 604/387, 389

[56] References Cited

U.S. PATENT DOCUMENTS

| | | | |
|---|---|---|---|
| 5,098,422 | 3/1992 | Davis et al. | 604/387 |
| 5,281,209 | 1/1994 | Osborn, III et al. | |
| 5,558,662 | 9/1996 | Van Iten | 604/387 |
| 5,704,931 | 1/1998 | Holtman et al. | 604/387 |

FOREIGN PATENT DOCUMENTS 0 337 438  10/1989  European Pat. Off. .
0 446 818   9/1991  European Pat. Off. .
2 244 910  12/1991  United Kingdom .

*Primary Examiner*—Mark O. Polutta
*Attorney, Agent, or Firm*—Young & Thompson

[57] ABSTRACT

An absorbent article, such as a sanitary napkin, a panty pad or a guard for persons afflicted with light incontinence, intended to be worn in the crotch part of underwear and having a generally elongated shape which includes two long sides (5, 6), two short sides (7, 8), two end parts (10, 11), a central part (9) between the end parts, a liquid-permeable sheet (2) intended to face towards the wearer's body, a liquid-impermeable sheet (3) intended to face away from the wearer's body, and an absorbent layer (4) located between these sheets, wherein the article further includes a main body (1) and at least two fastener flaps (12, 13) located on the liquid-impermeable sheet of the article, wherein the flaps are arranged to take a first use position A in which they form an angle α to the liquid-impermeable sheet (3), wherein in addition to the first use position A the flaps (12, 13) are also arranged to take a second use position B in which they lie against the liquid-impermeable sheet (3), and wherein the flaps (12, 13) are able to swing between their first use position A and their second use position B.

7 Claims, 4 Drawing Sheets

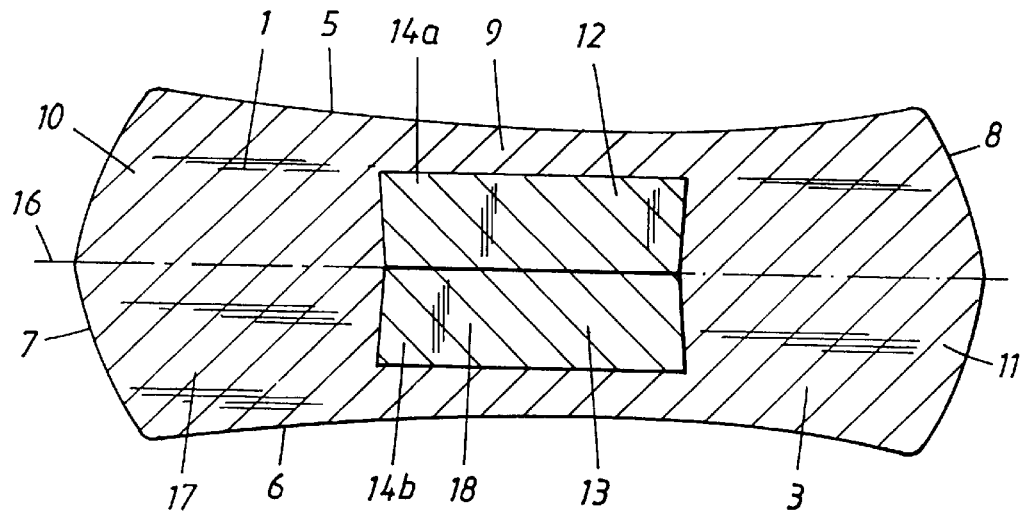
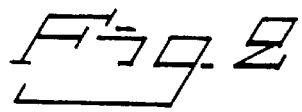
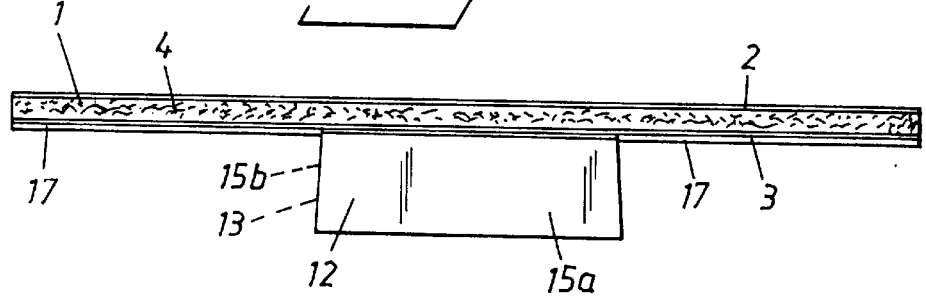
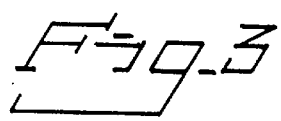
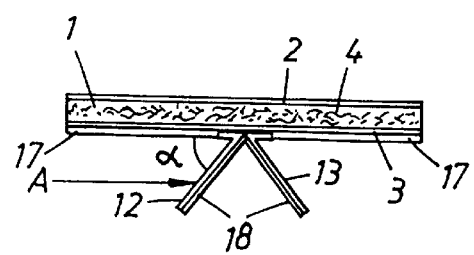

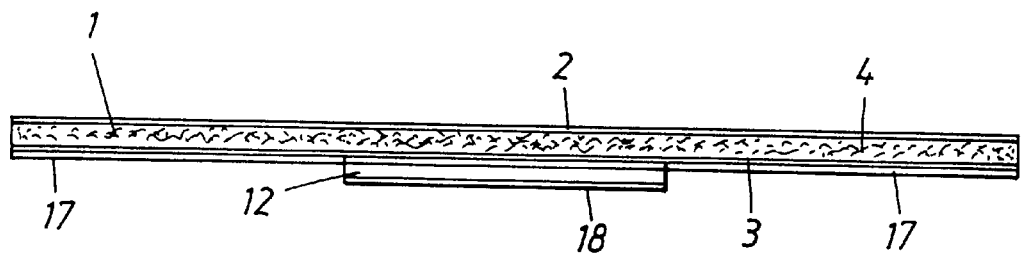
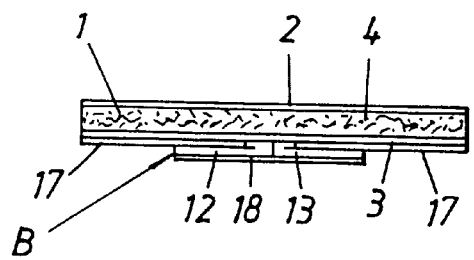
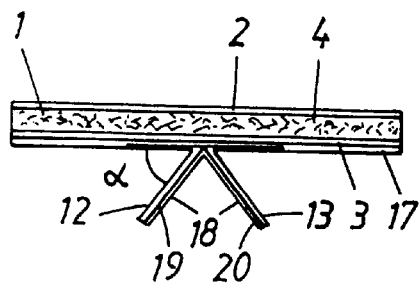

ABSORBENT ARTICLE FOR ATTACHMENT TO A BOXER SHORT OR A PANTY

FIELD OF INVENTION

The present invention relates to an absorbent article, such as a sanitary napkin, a panty pad or a guard for persons afflicted with light incontinence, wherein the article is intended to be supported in the crotch part of the wearer's underwear and has a generally elongated shape with two long sides, two short sides, two end parts, a center part located between said end parts, a liquid-permeable layer which is intended to lie proximal to the wearer's body, a liquid-impermeable layer which is intended to lie distal to the wearer's body, an absorbent layer located between these layers, and wherein the article includes a main body and at least two fastener flaps or wings located on the liquid-impermeable layer of said article.

DESCRIPTION OF THE BACKGROUND ART

Panty pads and mini-napkins are normally used at the end of a menstruation period when the discharge of body fluid is slighter, or between menstruation periods with the intention of collecting any fluid discharges that may occur. Persons afflicted with light incontinence may need to use incontinence guards more or less continuously. Persons afflicted with light incontinence have, in the main, control over their bladder emptying processes and only a few drops of urine will be discharged inadvertently. Drip incontinence is an example of light incontinence caused by the difficulty of an incontinent person, normally a male, to completely empty the urethra after urinating. Another type of light incontinence normal among women can occur as a result of physical strain, for instance when running, jumping, coughing and sneezing.

An absorbent article such as a sanitary napkin, an incontinence guard or a panty pad will normally include a liquid-permeable casing sheet, a liquid-impermeable sheet and an absorbent body placed therebetween. The liquid-permeable casing sheet is provided on that side of the absorbent article which is intended to lie proximal to the wearer's body, whereas the liquid-impermeable sheet is provided on that side of the article which is intended to lie distal from the wearer's body.

Sanitary napkins, panty pads and incontinence guards are normally fastened in the crotch of the wearer's underwear with the aid of adhesive applied in strips or other patterns on the rear side of the liquid-impermeable sheet. These adhesive surfaces are protected during storage and transportation prior to use by protective strips which are treated with a release agent and which are removed by the user in conjunction with placing the absorbent article in the underpants.

In order to enable the absorbent article to be removed from the wearer's underpants, it is necessary to balance the adhesive capacity of the adhesive against its release capacity. As a result, the article may slip from the wearer's underwear, either completely or partially, creating a problem for the user. It is highly probable that the article will become wrinkled even if it slips only slightly. This will result in the leakage of body fluid onto the wearer's underwear, primarily on the edges thereof.

It is known to solve this problem by providing the absorbent article with side flaps or wings which project out from the long sides of the article. These side flaps, or wings, are intended to be folded around the edge of the user's underpants, and fastened to the outside thereof, normally with the aid of adhesive applied to the rear side of the flaps. The flaps thus reduce the leakage of body fluid onto the wearer's underpants, partly by physically protecting the edges of the underpants and partly by providing more secure attachment of the article to the wearer's underpants. Fastener flaps of this kind are described in SE 455 668, U.S. Pat. No. 4,285,343, EP 130 848, EP 134 086 and U.S. Pat. No. 4,608,047, among others.

The aforedescribed side flaps function well in those cases when the underpants in which the article is to be fastened has a crotch part which is sufficiently narrow for the flaps to pass therearound to an extent sufficient to provide the flaps with a satisfactory grip. However, if the underpants have a very wide crotch part which is not generally flat, as in the case of boxer shorts for instance, the aforedescribed construction will fail.

OBJECT OF THE INVENTION

The object of the invention is to alleviate the aforesaid problems and to provide an absorbent article having a fastener system which will function with all types of underpants.

BRIEF DESCRIPTION OF THE INVENTION

An article of the aforedescribed kind with which problems associated with earlier known articles of this nature have been essentially alleviated is characterized in accordance with the invention in that the flaps are arranged to take a first use position A in which they define an angle α with the liquid-impermeable sheet; and in that the flaps are also arranged to take a second use position B in which they lie against the liquid-impermeable sheet; and in that the flaps can be swung between their first and their second use positions A and B respectively.

According to alternative embodiments of the invention, the flaps have an outside, an inside and are attached to the liquid-impermeable sheet of the main body at a distance from the long sides of said article and are provided with fastener means which are intended to be fastened to the wearer's underwear, and in that the flaps are resilient around their first position A and the absorbent layer includes at least one dry-formed sheet containing 5–100% cellulose fibre, said sheet having a density of between 0.2 and 1.0 g/cm$^3$ and a surface weight per unit area of between 30 and 2000 g/m$^2$, said sheet having been formed by compression of a web containing cellulose fibre without subsequent defibration and fluff formation.

DESCRIPTION OF THE INVENTION

The present invention solves the problem of fastening an absorbent article to underpants of mutually different crotch widths.

This is achieved by fastening the flaps to that side of the article which presents a liquid-impermeable surface, instead of fastening flaps to the side edges of the articles and wrapping the flaps around the edges of the underpants as in the earlier known case.

The risk of any fluid liquid that may be absorbed outside the central part of the article leaking through the rear side thereof can be further reduced by mixing superabsorbent in the absorbent material in the end parts of the article. By superabsorbent is meant polymeric absorbent materials in the form of powder, particles, granulates, film or the like that can absorb liquid in an amount corresponding to several times the weight of the polymeric material while forming an aqueous gel. The superabsorbent prevents liquid from spreading in the absorbent body, by absorbing and chemically binding the liquid. The superabsorbent thus functions both as an absorbent and as a barrier against leakage from the absorbent article.

Because the article is held in position on the wearer's underpants with the aid of article-carried side flaps, the article will not slide out of position or become wrinkled. Fluid discharged by the wearer will therefore impinge on the central part of the article and be absorbed by that part of the absorbent body which lies between the flaps.

With the intention of preventing fluid from leaking over the side edges of the article with resultant soiling of the wearer's clothes, it may be convenient to provide edge leakage barriers along the longitudinal side edges of the article. Such edge leakage barriers may have compressed regions of different patterns, for instance compressed patterns produced by mechanical or thermomechanical compression, or with the aid of ultrasound. Edge leakage barriers can also be formed by melting thermoplastic material in the article casing sheet or in the absorbent body with the aid of heat or ultrasound, so as to form liquid-impervious barriers along the longitudinal side edges of the article. The thermoplastic material may be a thermoplastic film or may comprise fibres or particles incorporated in a nonwoven casing sheet or admixed with the absorbent body. Liquid or fluid barriers may also be produced by applying a liquid-resistant adhesive along the edge parts of the absorbent body or by admixing superabsorbent with said edge parts. Such superabsorbents function to bind the absorbed body fluid and thereby to prevent transportation of the fluid beyond the side edges. An obstacle to the passage of body fluid beyond the side edges of the article can also be obtained by forming slots or notches in the absorbent material along the side edges of the article.

If considered appropriate, corresponding fluid barriers can be provided transversely of the longitudinal direction of the article so as to limit spreading of fluid in the longitudinal direction of the article. These fluid barriers can be provided between the central part and the end parts of the article, for instance.

The invention will now be described in more detail with reference to exemplifying embodiments thereof and also with reference to the accompanying drawings. It will be understood that the invention is not restricted to the embodiments illustrated in the drawings and that these embodiments are intended solely to illustrate and explain the principles of the invention.

BRIEF DESCRIPTION OF THE DRAWINGS

FIG. 1 illustrates a sanitary napkin from that side of the napkin which is intended to lie distal from the wearer.

FIG. 2 illustrates the napkin from one long side thereof with the flaps disposed in a first use position.

FIG. 3 illustrates a sanitary napkin from one short side thereof with the flaps disposed in a first use position.

FIG. 4 illustrates a sanitary napkin from one long side thereof with the flaps disposed in a second use position.

FIG. 5 illustrates a sanitary napkin from one short side thereof with the flaps disposed in a second use position.

FIG. 6 illustrates a sanitary napkin according to an alternative embodiment of the invention, and shows the napkin from one short side thereof with the flaps disposed in a first use position.

DETAILED DESCRIPTION OF DRAWINGS AND EMBODIMENTS

Figure 7:
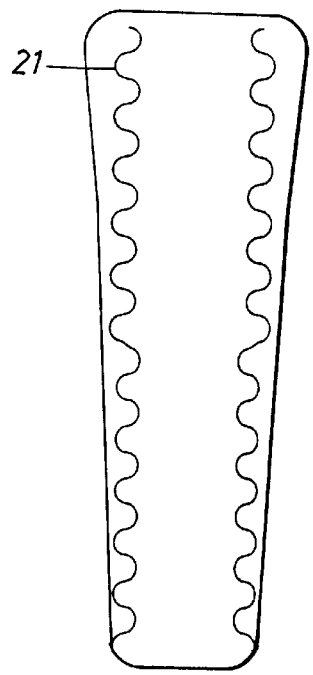
FIGS. 7–14 illustrate sanitary napkins having mutually different leakage barriers.

The sanitary napkin illustrated in the drawings includes a main body 1 that has a liquid-permeable sheet 2 on that side of the main body which lies proximal to the wearer in use, a liquid-impermeable sheet 3 on that side which is intended to lie distal from the wearer in use, and an absorbent layer 4 located between the aforesaid sheets.

The main body 1 has an essentially oblong shape and is defined in the plane by two long sides 5, 6 and two short sides 7, 8. The sanitary napkin also includes a central part 9 disposed in the longitudinal direction of the article between its two end parts 10, 11. Each of the central part 9 and end parts 10, 11 take up approximately one-third of the length of the article.

The liquid-impermeable sheet or back sheet 3 is comprised of liquid-impervious material. Thin, liquid impervious plastic films are suitable for this purpose, although it is possible to use initially liquid permeable material that has been provided with a layer of plastic, resin or some other liquid impervious material. This prevents leakage of liquid from the backside of the absorbent article. The back sheet 3 may be comprised of any material that fulfils the liquid-impermeability criterion and is sufficiently flexible and skin-friendly for the purpose intended. Examples of materials suitable as sheets are plastic films, nonwoven and laminates thereof. The plastic film may be comprised of polyethylene, polypropylene or polyester. Alternatively, the back sheet may be comprised of a laminate of a liquid-impermeable plastic layer facing towards the absorbent body and a nonwoven layer facing towards the wearer's underpants. This construction provides a leakage-safe back sheet having a fabric-like feel.

The absorbent layer 4 is suitably comprised of cellulose pulp. The pulp may be in roll form, in bales or in sheets that have been dry-defibrated and converted to a fluffed state in a pulp mat, at times while admixing the pulp with so-called superabsorbents which, as before mentioned, are polymers that are capable of absorbing water or body fluid in quantities corresponding to several times their own weight. Examples of other materials that can be used in this context are different types of natural fibres, such as cotton fibres, peat moss or the like. Naturally, the use of absorbent synthetic fibres or mixtures of natural fibres and synthetic fibres is also conceivable. The absorbent material may also contain other components, such as shape-stabilizing agents, liquid dispersing agents or binding agents, such as thermoplastic fibres that have been heat-treated to hold together short fibres and particles in a coherent unit. It is also known to use different types of absorbent foam material in the absorbent body.

The absorbent layer 4 of the sanitary napkin is covered by a liquid-permeable top sheet 2 provided on that side of the main body 1 which faces towards the wearer in use. The top sheet 2 may be comprised of perforated plastic film, plastic or textile net, nonwoven material or a laminate comprised of a plastic layer and a nonwoven layer, for instance. The plastic may be a thermoplastic, such as polyethylene. The nonwoven material may be comprised of natural fibres, such as cellulose or cotton, or synthetic fibres, such as polyethylene, polypropylene, polyester, polyurethane, nylon or regenerated cellulose fibres.

The main purpose of the casing sheet 2 of the sanitary napkin is to guide fluid into the absorbent layer 4, to be soft and comfortable against the wearer's body, and to prevent so-called rewetting, i.e. the return of absorbed body fluid onto the wearer's skin. With regard to comfort and the avoidance of skin irritations, it is important that the surface of that part of the napkin which lies against the wearer's skin remains as dry as possible in use. A dry napkin surface is also felt to be more cool and comfortable by the user, and is more attractive than a soiled, wet surface when changing the napkin, both from a purely visual aspect and from a handling aspect.

The article also includes two fastener flaps 12, 13, each having an inside 14*a,b* and an outside 15*a,b* for fastening the article to the wearer's underclothes. The flaps 12, 13 are fastened to the main body 1 of the napkin, for instance glued, welded or sewn, on that side of the body which presents the fluid impermeable sheet 3. The flaps are fastened to the fluid impermeable sheet 3 of the main body at a distance from the long sides 5, 6 of the article. The flaps are preferably fastened in the center of the rear side of the article, as seen from the short sides 7, 8 thereof, although the flaps may alternatively be fastened closer to the long sides of said article while maintaining a good fastener function in the V-shaped crotch part of underwear. When the width of the article in that part where the flaps or wings are fastened, i.e. the central part 9, is 5 cm, the preferred distance from the long sides 5, 6 of the article will be about 2.5 cm. Naturally, these relationships are to scale: For instance, if the width of the central part is 8 cm, then the preferred distance from the long sides of the article will be 4 cm. In the illustrated case, the flaps 12, 13 are fastened adjacent one another on the fluid or liquid impermeable sheet 3. Alternatively, the flaps 12, 13 may be fastened closer to the long sides 5, 6 of the article and not positioned adjacent one another. For instance, when the width of the article is 5 cm, the flaps 12, 13 may be fastened at a distance of 1.5 cm from each long side 5, 6. When the width of the article is 8 cm, the flaps 12, 13 may be fastened at a distance of 3 cm from the long sides of the article.

FIGS. 1–3 illustrate an article having fastener flaps 12, 13 disposed in a first use position A in which they define an angle α with the liquid-impermeable sheet 3. When the sanitary napkin is in an initial state of its application, the first use position A can be described as a position in which the flaps 12, 13 extend obliquely outwards from the back sheet 3 in a direction away from the longitudinal symmetry line 16 of the napkin and towards respective long sides 5, 6, such as to define an angle α. In other words, the angle α is defined between the extension direction of respective fastener flaps 12, 13 and the napkin back sheet. FIGS. 4–5 illustrate a sanitary napkin with the fastener flaps 12, 13 disposed in a second use position B. In use position B, the fastener flaps, or wings, lie against the back sheet 3 without defining an angle thereto. The first use position A shown in FIGS. 1–3 is suitable for mounting the sanitary napkin in boxer shorts, panty hose and similar types of underwear that have a broad, V-shaped crotch. The second use position B shown in FIGS. 4–5, is suitable for mounting the sanitary napkin in underwear that have a generally flat crotch part. The first use position A makes an angle α between the flaps 12, 13 and the liquid-impermeable sheet 3, this angle depending on the steepness of the V-shape of the crotch part. The angle a will vary with the body attitude of the wearer and his/her movements thereof and also according to the nature of the underwear in which the article is mounted. The angle a will vary between 0 and 90°. The angle will be relatively large, about 45–90° when the sanitary napkin is mounted in boxer shorts made of loose, flexible material, whereas when the napkin is mounted in panty hose, the angle will be smaller and in the region of 0–45°. Naturally, this data is approximate with regard to the position of the flaps 12, 13 in relation to the liquid-impermeable sheet 3 and thereby to the main body 1. The angle a will also vary in dependence on the movements and body attitudes of the wearer. However, the flaps will be resilient or elastic around the use position.

The first use position A primarily places special requirements on the article. In order to ensure that the main body 1 will not wrinkle or gather together when in use, the main body must be rigid or stiff. This is achieved by using one or more stiff layer, for instance a stiff liquid-permeable sheet 2, a stiff liquid impermeable sheet 3 or a stiff absorbent layer 4 in the main body 1, or by including stiff layers in the main body 1. One simple method of obtaining a stiff main body 1 which will not wrinkle in use is to form the absorbent layer 4 from a stiff material. A suitable material with regard to the absorbent layer 4 is the absorbent material described in WO 94/10956. This material is a dry-formed fibre sheet of high density and stiffness that can be used directly in an absorbent article without first being defibrated. A similar material having particularly suitable blood-absorption properties is described in WO 94/10953. Both of these materials have sufficient stiffness and ability to withstand deformation and therewith impart to the main body 1 the shape stability required by the present invention.

Rigid absorbent material of the aforesaid nature may be comprised of dry-formed sheet containing 5–100% cellulose fibre and having a density of between 0.2 and 1.0 g/cm$^3$ and a weight by surface area of between 30 and 2000 g/m$^2$, wherein the sheet is formed by compressing a web that contains cellulose fibres without subsequent defibration and fluff formation. Since this material absorbs liquid relatively slowly, it may be appropriate to include in the absorbent layer 4 additional absorbent material which will absorb more rapidly, this material being placed nearest the liquid-permeable sheet 2. Air-laid material is an example of such rapid absorbent material.

It may be beneficial for the fastener flaps 12, 13 to be resilient in their first use position A. The resilience of the flaps 12, 13 around their use position A may also be beneficial when the sanitary napkin is used with the flaps 12, 13 in their second use position B. If the flaps 12, 13 are not fastened to the back sheet 3, the resiliency will cause the main body 1 to be pressed resiliently against the wearer's body therewith reducing the risk of the napkin gaping away from the wearer's skin and resulting in a more leakage-proof sanitary napkin. An elastic effect can be obtained by providing the main body 1 and the flaps 12, 13 with elastic threads 19, 20, which are mounted in a stretched state. One such construction is shown in FIG. 6. In this case, it may be convenient to cover the whole of the back sheet 3 with an area of pressure-sensitive adhesive 17. This will enable the flaps 12, 13 to be fastened to the back sheet 3 and the article to be used in its second use position B. If the user wishes to use the article with its flaps 12, 13 in their first use position A, the flaps 12, 13 are released from the back sheet 3 and spring back around to the first use position A. Alternatively, the outer surfaces 15*a,b* of the fastener flaps may be provided with a pressure-sensitive adhesive, instead of covering the whole of the back sheet 3 with said adhesive area 17.

The fastener means 17, 18 are comprised of self-adhesive surfaces, although other types of fasteners may be used, such as hook-and-loop fasteners or other types of fastener which can be fastened directly to the materials from which panties or underpants are normally made.

FIGS. 1–5 illustrate an example of how the fastener means can be applied. The fastener means 17, 18 are comprised of pressure-sensitive adhesive applied to the liquid-impermeable sheet 3 and on the inner surface 14a,b of the fastener flaps 12, 13. The fastener means are shown hatched in FIG. 1. The adhesive surface 17 applied to the liquid-impermeable sheet is used solely to fasten the article when said article is to be placed in underwear that have a substantially flat crotch region, in other words when the flaps 12, 13 are in their second use position B. In this case, the adhesive surface 18 on the inner surfaces 14a,b of the flaps is also used to fasten the article to the wearer's underwear. When the article is to be secured in underwear that have a V-shaped crotch region, such as boxer shorts, only the adhesive surface 18 on the inner surfaces 14a,b of the flaps is used. Naturally, it is not necessary to cover the whole of the liquid-impermeable sheet 3 with adhesive and it is conceivable to apply adhesive solely to the flaps 12, 13, i.e. the adhesive surface 18.

Although not shown in the drawings, the fastener means 17, 18 are covered with releasable protective paper prior to use, this paper being removed from the fastener means 17, 18 before use. The protective paper or like means may be omitted when the fastener means 17, 18 are comprised of a material which will not adhere spontaneously to other surfaces or when the fastening capacity is not impaired after being released from such spontaneous adherence to another surface.

The article may be provided with edge leakage barriers 21, so as to reduce the risk of leakage from the article. FIGS. 7–14 illustrate different embodiments of these barriers. The edge leakage barriers may extend along the full length of the absorbent body or may solely cover the central part of the napkin.

Figure 8:
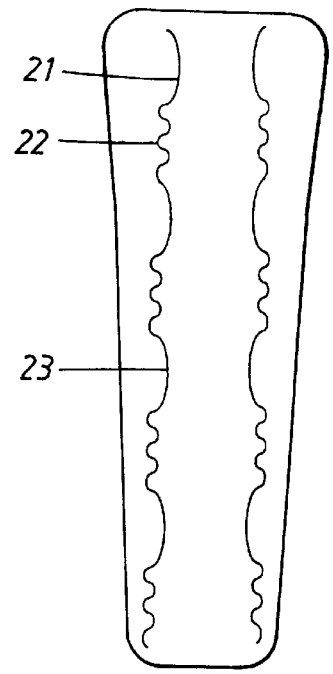
Figure 9:
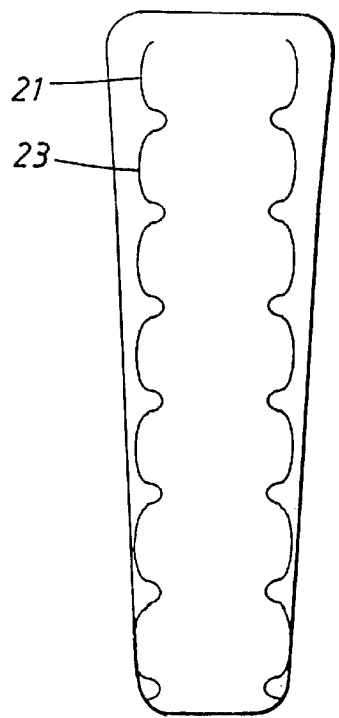
Figure 10:
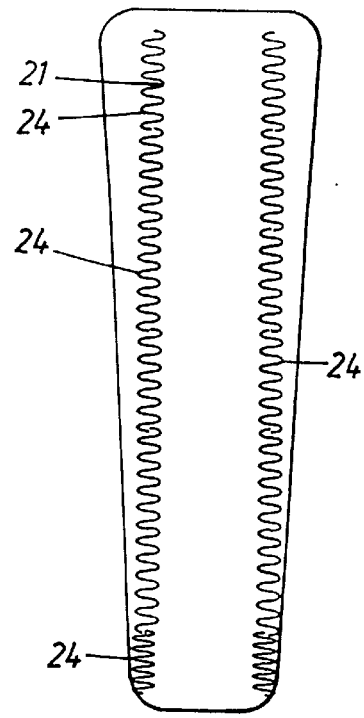
Figure 11:
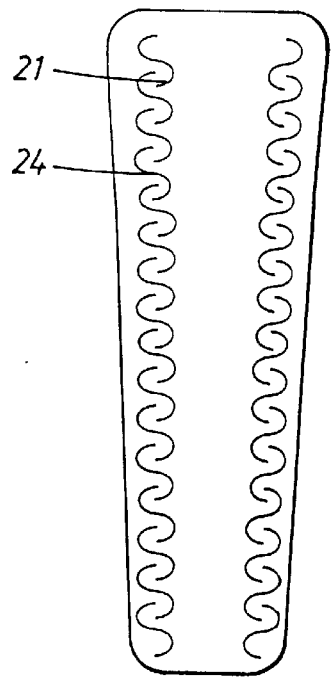
Figure 12:
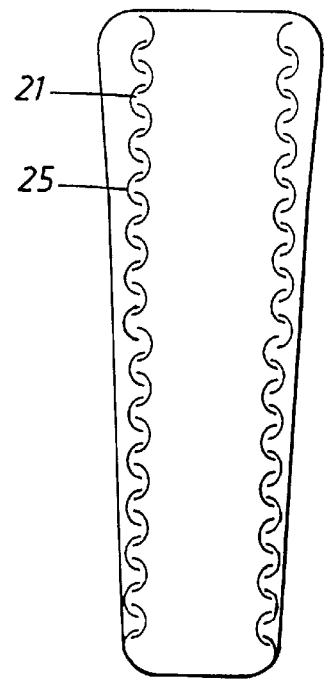
Figure 13:
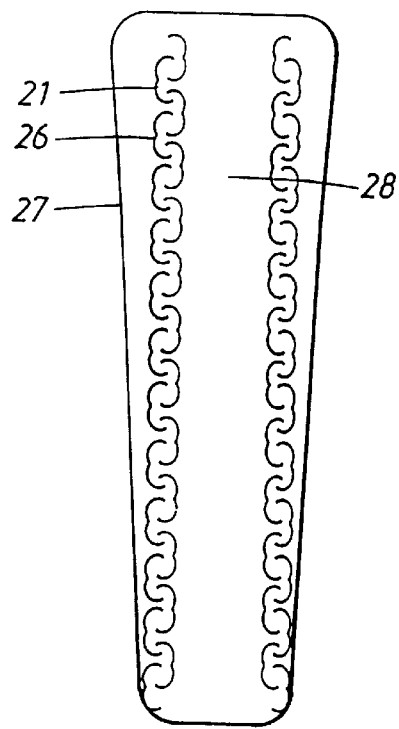

FIGS. 7 and 10 illustrate edge leakage barriers 21 of sinusoidal configuration. FIG. 8 illustrates edge leakage barriers having two different repeating patterns alternating. A sinusoidal wave pattern 22 is interrupted by an arcuate section 23 on the edge leakage barrier 21. The edge leakage barriers 21 as shown in FIG. 8 have only arcuate sections 23. FIG. 11 illustrates edge leakage barriers 21 that have an interrupted pattern. Each interrupted part has an S-shape 24. These S-shaped sections 24 overlap slightly and sequentially in a generally straight row or column and together form the edge leakage barriers 21. FIGS. 12 and 13 also illustrate edge leakage barriers that have an interrupted pattern. The edge leakage barriers 21 shown in FIG. 12 are comprised of a repeating pattern of semi-circles 25 somewhat overlapping each other. The edge leakage barriers 21 shown in FIG. 13 are comprised of a repeating E-shaped pattern 26. The E-shaped sections 26 overlap one another and are disposed so that the openings alternately point towards the napkin edge 27 and alternately towards the center 28 of the napkin.

That side of the absorbent article which is intended to lie proximal to the wearer's body in use may also be provided with transversely extending leakage barriers, so as to prevent spreading of fluid or liquid in a longitudinal direction.

Figure 14:
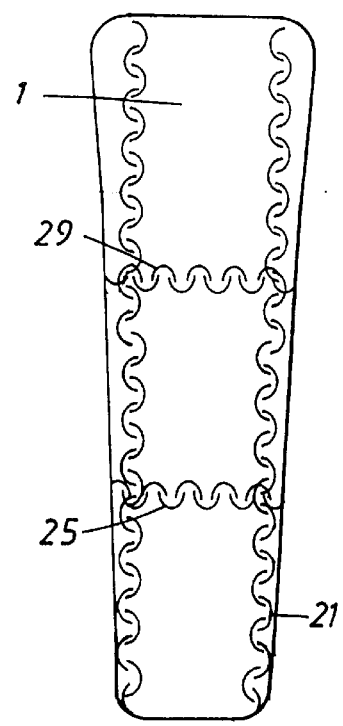

FIG. 14 illustrates leakage barriers 29 placed transversely on a sanitary napkin, for instance. The transverse barriers have the same pattern 25 as that used for the edge leakage barriers 21 of the FIG. 11 embodiment. It will be understood that this is solely an example and that all patterns suitable as edge leakage barriers 21 and shown in FIGS. 6–12 can be equally as well used in producing transversal leakage barriers 29 of the same configuration as the edge leakage barriers 21.

The aforedescribed leakage barriers are solely examples of possible configurations and other patterns or configurations are conceivable. Naturally, the main purpose of the barrier configuration is to impede the passage of fluid beyond the barrier pattern while not resulting in a stiff or skin-chafing product. The aforedescribed and illustrated patterns can also be used for purposes other than to provide a leakage-proof product. For instance, they can be used to stiffen the article when so required or to shape the article, for instance impart a three-dimensional shape thereto.

The invention has been described above with reference to a sanitary napkin for the sake of simplicity. It will be understood, however, that the illustrated and described embodiment can also equally apply to light incontinence guards, panty pads or like absorbent articles embraced by the inventive concept.

I claim:

1. An absorbent article, selected from the group consisting of a sanitary napkin, a panty pad, and a guard for persons afflicted with light incontinence, intended to be worn by a wearer in the crotch part of underwear, the article comprising:

a main body having a generally elongated shape which includes two long sides generally extending in the direction of a longitudinal first axis, two short sides generally extending in the direction of a second axis which is transverse to said first axis, a plane extending through said first axis, said plane being perpendicular to said second axis, two end parts, a central part between said end parts, a liquid-permeable sheet intended to face towards the wearer's body, a liquid-impermeable sheet intended to face away from the wearer's body, an absorbent layer located between said sheets, and at least two fastener flaps including a first flap extending from said liquid-impermeable sheet to a distal first flap edge and a second flap extending from said liquid-impermeable sheet to a distal second flap edge, said first and second flaps being pivotal relative to said body about a pivotal axis which is substantially parallel to said longitudinal axis, said first and second flaps (a) extending at an angle $\alpha$ relative to said transverse axis in a first use position, and (b) being substantially parallel to said transverse axis in a second use position; said first and second flap distal edges facing away from said plane in said first and second use positions.

2. The absorbent article according to claim 1, wherein said first and second flaps extend from said impermeable sheet at said pivotal axis.

3. The absorbent article according to claim 2, wherein said pivotal axis is centered between said two long sides.

4. The absorbent article according to claim 1, wherein each of the flaps have an inside and an outside.

5. The absorbent article according to claim 4, further comprising fastener means provided on the insides of the flaps for fastening said flaps to the wearer's underwear.

6. The absorbent article according to claim 1, wherein the flaps are resilient around their first use position.

7. The absorbent article according to claim 1, wherein the absorbent layer includes at least one dry-formed sheet containing 5–100% cellulose fiber and having a density of between 0.2 and 1.0 g/cm$^3$ and a weight per surface area of between 30 and 2000 g/m$^2$, said dry-formed sheet having been formed by compressing a web of cellulose fibers without subsequent defibration and fluff formation.

* * * * *